United States Patent [19]

Hopper et al.

[11] Patent Number: 5,068,185

[45] Date of Patent: Nov. 26, 1991

[54] TRAINS OF YEAST FOR THE EXPRESSION OF HETEROLOGOUS GENES

[75] Inventors: James E. Hopper, Lebanon; Loren D. Schultz, Harleysville; Kathryn J. Hofmann, King of Prussia; Ronald W. Ellis, Overbrook Hills, all of Pa.

[73] Assignee: Merck & Co., Inc., N.J.

[21] Appl. No.: 884,114

[22] Filed: Jul. 10, 1986

[51] Int. Cl.$^5$ .................. C12P 21/02; C12N 15/00; C12N 1/14; C12N 1/16; C12N 1/18; C12N 15/81; C12N 1/19
[52] U.S. Cl. .................. 435/69.1; 435/172.1; 435/254; 435/255; 435/256; 435/320.1; 935/28; 935/37; 935/56; 935/61; 935/69
[58] Field of Search .................. 435/172.3, 254, 255, 435/256, 320, 69.1; 935/28, 69, 37

[56] References Cited

PUBLICATIONS

Laughon et al., Mol. Cell Bio. vol. 4, pp. 268-275 (1984).

Primary Examiner—Richard A. Schwartz
Assistant Examiner—J. Ellis
Attorney, Agent, or Firm—Donald J. Perrella; Hesna J. Pfeiffer; Julian S. Levitt

[57] ABSTRACT

The GAL4 protein is rate-limiting in quantity as a positive regulator for galactose-inducible promoters in strains of yeast. Novel strains are described in which the GAL4 protein can be overproduced in a regulatable fashion. These strains are useful for the regulatable expression in yeast of heterologous genes whose expression is driven by a galactose-inducible promoter.

12 Claims, 8 Drawing Sheets

TRAINS OF YEAST FOR THE EXPRESSION OF HETEROLOGOUS GENES

BACKGROUND OF THE INVENTION

*Sacccharomyces cerevisiae* has proven versatile as a host species for the expression of foreign polypeptides. Many different proteins from a variety of species have been expressed in *S. cerevisiae*, some to levels of >10% of total cell protein. Typically, expression has been mediated by a plasmid containing yeast regulatory sequences (transcriptional promoter and terminator) circumscribing the structural gene for the expressed polypeptide as well as other sequences required for the selection and amplification of plasmids in both *S. cerevisiae* and in *Escherichia coli*. In addition, it has been possible to integrate the yeast regulatory sequences circumscribing the structural gene for the expressed polypeptide into a yeast chromosome and achieve high-level expression.

*S. cerevisiae* has 4 genes which encode the enzymes responsible for the utilization of galactose as a carbon source. The GAL1, GAL2, GAL7, and GAL10 genes respectively encode galactokinase, galactose permease, α-D-galactose-1-phosphate uridyltransferase, and uridine diphosphogalactose-4-epimerase. In the absence of galactose, very little expression of these enzymes is detected. If cells initially are grown on medium containing glucose, and galactose is added to the culture, these four enzymes are induced coordinately by at least 1000-fold upon depletion of glucose from the media. This induction has been shown to occur at the level of RNA transcription. The GAL1, GAL2, GAL7 and GAL10 genes have been molecularly cloned and sequenced. The regulatory and promoter sequences to the 5' sides of some of the respective coding regions have been placed adjacent to the coding regions of the lacZ gene. These experiments have defined those promoter and regulatory sequences which are necessary and sufficient for galactose induction and which are useful for driving the expression of heterologous genes.

The GAL4 and GAL80 gene products are respectively positive and negative regulators of the expression of the GAL1, GAL2, GAL7, and GAL10 genes as well as of the MEL1 gene, which encodes α-galactosidase, an enzyme required for melibiose catabolism. The GAL4 product acts as a positive regulator at the transcriptional level by binding to specific DNA sequences 5' to the structural information of these genes. In the absence of galactose, the GAL80 gene product (protein) interacts with the GAL4 gene product or with a DNA sequence to prevent this transcriptional activation event. In the presence of galactose, the GAL80 protein apparently cannot antagonize the GAL4 protein, and the GAL4 protein can function as a transcriptional activator. The GAL4 gene is expressed at very low levels, and its product is rate-limiting for the optimal induction of the GAL gene promoters. This is especially true when a cell contains multiple copies of plasmids with galactose-inducible promoters driving the expression of heterologous genes. However, if it is a goal to maintain minimal or no expression of a heterologous gene before the addition of galactose, it is important that the GAL4 gene be expressed at very low levels in the absence of galactose.

In a variety of recombinant microbial expression systems, the synthesis of many different heterologous polypeptides has been shown to be deleterious to the host cell. As a consequence, there is selective pressure against the expression of such heterologous polypeptides, such that the only cells which accumulate in a scale-up of such a recombinant culture are those which do not express the heterologous polypeptide or express so little of the heterologous polypeptide that the culture becomes an uneconomical source of that polypeptide. An optimal scheme for the scale-up of such a recombinant culture would be to maintain minimal or no expression of the heterologous gene during the expansion of the culture to a large volume and high cell density and then to induce the maximal expression of the heterologous gene only in the final stage of culture growth prior to product isolation.

OBJECTS OF THE INVENTION

It is an object of the present invention to provide novel strains of yeast in which the GAL4 protein can be overproduced in a regulatable fashion, such that the expression of heterologous genes driven by galactose-inducible promoters can be minimized during the expansion of the culture to a high cell density and maximized at the final stage of culture growth prior to product isolation. This and other objects of the present invention will be apparent from the following description.

SUMMARY OF THE INVENTION

The GAL4 protein is rate-limiting in quantity as a positive regulator for galactose-inducible promoters in strains of yeast. Novel strains are described in which the GAL4 protein can be overproduced in a regulatable fashion. These strains are useful for the regulatable expression in yeast of heterologous genes whose expression is driven by a galactose-inducible promoter.

DETAILED DESCRIPTION OF THE INVENTION

The present invention is directed to the development of novel strains of yeast in which the GAL4 gene product can be overexpressed in a regulatable fashion. The present invention also is directed to the use of such novel strains as a host for the expression of heterologous genes driven by a galactose-inducible promoter. Specifically, it is directed to conditions for the scale-up of such recombinant cultures such that heterologous gene expression can be minimized during the expansion of the culture to a large volume and high cell density and then maximized at the final stage of culture growth prior to product isolation.

An expression cassette, containing the GAL10 promoter fused to the GAL4 structural gene, is constructed in such a way that cells which integrate this cassette at the HIS3 locus can be selected. The *E. coli—S. cerevisiae* shuttle vector YEp51 contains the yeast GAL10 promoter sequences. This plasmid is digested with Sau3A and SalI, and the 0.5 kbp GAL10 promoter fragment is isolated by preparative agarose gel electrophoresis. Two oligonucleotide linkers are synthesized and ligated to the 0.5 kbp fragment, thus converting the 5' Sau3A and the 3' SalI ends to EcoRI and BglII ends, respectively. After subsequent digestion with EcoRI and BglII, the 0.5 kbp EcoRI-BglII GAL10 promoter fragment is isolated by preparative agarose gel electrophoresis. The yeast GAL4 structural gene (including the translational start site) is isolated from pSJ3 and subcloned to form pIA. This plasmid is digested with BamHI and HindIII, and the 2.9 kbp GAL4 fragment is isolated by preparative agarose gel electrophoresis. The plasmid vector pJJ42 contains the yeast HIS3 gene. This plasmid is digested with EcoRI and HindIII to remove a segment of the HIS3 gene extending from the middle of the coding region to just upstream of the HIS3 promoter. The 12 kbp vector fragment is isolated by preparative agarose gel electrophoresis and ligated simultaneously with the 0.5 kbp and 2.9 kbp fragments described above to yield the plasmid pKHint-A. The pGAL10/GAL4 expression cassette is removed from pKHint-A by digestion with BamHI, and the 5.6 kbp fragment is isolated by preparative agarose gel electrophoresis. The plasmid vector pJJ98, a modified pBR322 lacking the HindIII site, is digested with BamHI and ligated to the 5.6 kbp cassette. The resulting plasmid pKHint-B contains a unique HindIII site located beyond the carboxy-terminal end of the GAL4 coding sequence. The fully functional yeast URA3 gene is isolated from the *E. coli—S. cerevisiae* shuttle vector YEp24 by digestion with HindIII and separation of the 1.2 kbp fragment by preparative agarose gel electrophoresis. After digestion with HindIII, plasmid pKHint-B is ligated to the 1.2 kbp HindIII fragment carrying the URA3 gene to yield pKHint-C, which now contains the complete expression cassette for integration into the yeast chromosome. The salient features of this cassette are: 1) yeast requlatable GAL10 promoter, 2) yeast GAL4 translational start site and structural gene, 3) yeast URA3 promoter and structural gene for positive selection in ura3- yeast host, and 4) two BamHI sites which cleave within the 5' and 3' non-translated sequences of the HIS3 gene for integrative-replacement transformation into the yeast HIS3 locus.

When digested with BamHI, the plasmid pKHint-C yields a 6.8 kbp expression cassette flanked on either end by nontranslated HIS3 DNA sequences. The digested DNA is used to transform *S. cerevisiae* host strains Sc252 (MATa, ura3-52, leu2-2-112, adel, MEL1) and Sc294 (MATα, ura3-52, leu2-2-112, Δgal1-10-7, MEL1). Acting as a targeting device, the BamHI ends direct the expression cassette to the chromosomal HIS3 locus where the cassette integrates via homologous recombination. Transformants are selected for URA3+ and screened for his3-. Southern blot analysis of the clonal isolates, referred to as Sc252 (pGAL10//Gal4) and Sc294 (pGAL10/GAL4), confirms that the cassette has integrated at the HIS3 locus. Transformants and their respective parental strains are grown in glycerol-lactic acid medium either with or without 2% (w/v) galactose. After harvesting at $A^{600}=1.5$, RNA extracts are prepared and analyzed by Northern blot techniques. In the presence of galactose, transcription of GAL4 mRN is observed to be at least 20-fold enhanced in the Sc252 (pGAL10/GAL4) and Sc294 (pGAL10/GAL4) strains over their respective parental strains. The strains show basal-level expression of GAL4 mRNA in the absence of galactose. Thus, the novel yeast strains display the desired phenotype of basal-level GAL4 expression in the absence of galactose and the higher (than wild-type strains) level expression of GAL4 in the presence of galactose.

In order to test whether the novel yeast strains afford an enhancement over wild-type strains of the levels of expression of a heterologous gene, an expression vector containing a galactose inducible promoter is prepared for transforming the strains. The salient features of this plasmid are: 1)*Escherichia coli*-derived sequences for the selection and amplification of the plasmid in *E. coli*, 2) *S. cerevisiae*-derived sequences for the selection and amplification of the plasmid in yeast, 3) yeast GAL10 promoter, 4) yeast alpha mating factor pre-leader for directing the translational product into the rough endoplasmic reticulum, 5) yeast alpha mating factor pro-leader which encodes N-glycosylation signal sequences and which is cleaved by the KEX2 and STE13 proteases (gene products), 6) the coding sequence for the Epstein-Barr virus membrane antigen (EBMA) proteins, which are 350,000 and 220,000 dalton glycoproteins encoded by EB virus (EBV) and resident on the surface of EBV-infected cells and EB virions, 7) a translational termination sequence, and 8) a yeast transcriptional termination sequence. This recombinant plasmid is introduced to *S. cerevisiae* strains which are wild-type for GAL4 and to isogenic *S. cerevisiae* strains which are harboring the pGAL10/GAL4 integrant, and transformed clones are selected. Cells are grown in synthetic selective glycerol-lactic acid medium; galactose is added to the cultures to induce expression of the EBMA gene. RNA is prepared from both strains and subjected to Northern blot analysis. The mRNA encoding EBMA is amplified at least 4-5 fold in the pGAL10/GAL4 integrant over the wild-type strain. Lysates are prepared, electrophoresed in polyacrylamide gels, and Western blotted to nitrocellulose. EBMA proteins reactive specifically with human convalescent EBV sera are amplified approximately 10-fold in the pGAL10/GAL4 integrant over the wild-type strain. No EBMA mRNA or EBMA protein is detectable in the pGAL10/GAL4 integrant strain prior to the addition of galactose to the culture.

The GAL4 protein functions as a transcriptional activator of galactose-inducible promoters and does not a priori influence the way in which heterologous gene products whose expression is driven by galactose-inducible promoters would be translated or processed post-translationally. Therefore, it is obvious to those skilled in the art that the concept of utilizing a yeast strain in which the GAL4 protein can be overproduced in a regulatable fashion as a host for heterologous gene expression extends to any heterologous gene whose expression is driven from a galactose-inducible promoter. Furthermore, it is obvious to those skilled in the art that any one of the galactose-inducible promoters, GAL1, GAL2, GAL7, GAL10, or MEL1, all being subject to GAL4-mediated transcriptional activation, can be utilized to drive the expression of heterologous genes in a yeast host in which the GAL4 protein can be overproduced in a regulatable fashion. Another key concept is that the GAL4 protein overproduction should be regulatable, meaning that GAL4 gene expression should be driven by a promoter whose activity is regulatable by any physiological means, including but not limited to the addition of galactose to a culture. Therefore, it is obvious to those skilled in the art that a novel strain in which the GAL4 protein can be overproduced in a regulatable fashion would contain a GAL4 gene whose expression is driven by a promoter other than one which is galactose-inducible, including but not limited to the promoters of the alcohol dehydrogenase 2, acid phosphatase, phosphoglycerate kinase, invertase, yeast heat shock and copperthionein genes. Furthermore, it is obvious to those skilled in the art that those sequences containing a regulatable promoter and the GAL4 coding sequence can reside in the yeast host either in an integrated form or on a plasmid and still allow for the regulatable overproduction of the GAL4 protein.

The genus Saccharomyces is composed of a variety of species. Most commonly used is *Saccharomyces cerevisiae*, or baker's yeast, as a host for the recombinant-DNA mediated expression of a variety of foreign polypeptides. However, the distinctions among the other species of the genus Saccharomyces are not always well-defined. Many of these species are capable of interbreeding with *S. cerevisiae* and have been demonstrated to possess galactose-inducible genes and positive regulatory proteins for the transcriptional activation of such genes. The positive regulator, which in *S. cerevisiae* is known as GAL4, may be of different structure or name from GAL4 and still function as a transcriptional activator of galactose-inducible promoters. Therefore, it will be obvious to those skilled in the art that the concept of utilizing a strain in which the GAL4 protein, or other positive regulator for transcriptional activation of galactose-inducible promoters, can be overproduced in a regulatable fashion and can be extended to other species of the genus Saccharomyces, including but not limited to carlsbergensis, norbensis, diastaticus, oviformis, uvarum, rouxii, montanus, kluyveri, and elongisporus.

Several yeast genera, such as Hansenula, Candida, Torulopsis, and Pichia, have been shown to contain similar metabolic pathways for the utilization of methanol as a sole carbon source for growth. The gene for alcohol oxidase, an enzyme which participates in this metabolic pathway, has been isolated from *Pichia pastoris*. The *P. pastoris* alcohol oxidase promoter has been isolated and shown to be sensitive to methanol induction of expression. The promoter has been placed on an expression vector, where it has been shown to promote the expression of foreign genes cloned adjacent to it. Thus, the principle of utilizing an inducible promoter to direct expression of foreign genes in species of other yeast genera is well-established. Moreover, species of other yeast genera can utilize a variety of carbon sources, including galactose, for growth. Therefore, it will be obvious to those skilled in the art that the concept of increased and regulated expression of a positive regulatory element as a transcriptional activator of galactose inducible promoters to increase expression of a heterologous gene whose expression is driven by a galactoseinducible promoter extends the range of suitable yeast hosts to species of yeast from the families Saccharomycetaceae and Cryptococcaceae, including but not limited to species from the genera Pichia, Candida, Hansenula, Torulopsis, Kluyveromyces, and Saccharomycopsis.

The following examples illustrate the present invention without, however, limiting the same thereto. The disclosure of each reference mentioned in the following examples is hereby incorporated by reference.

EXAMPLE 1

Preparation of a pGAL10/GAL4 expression cassette for integrative transformation

Figure 1:
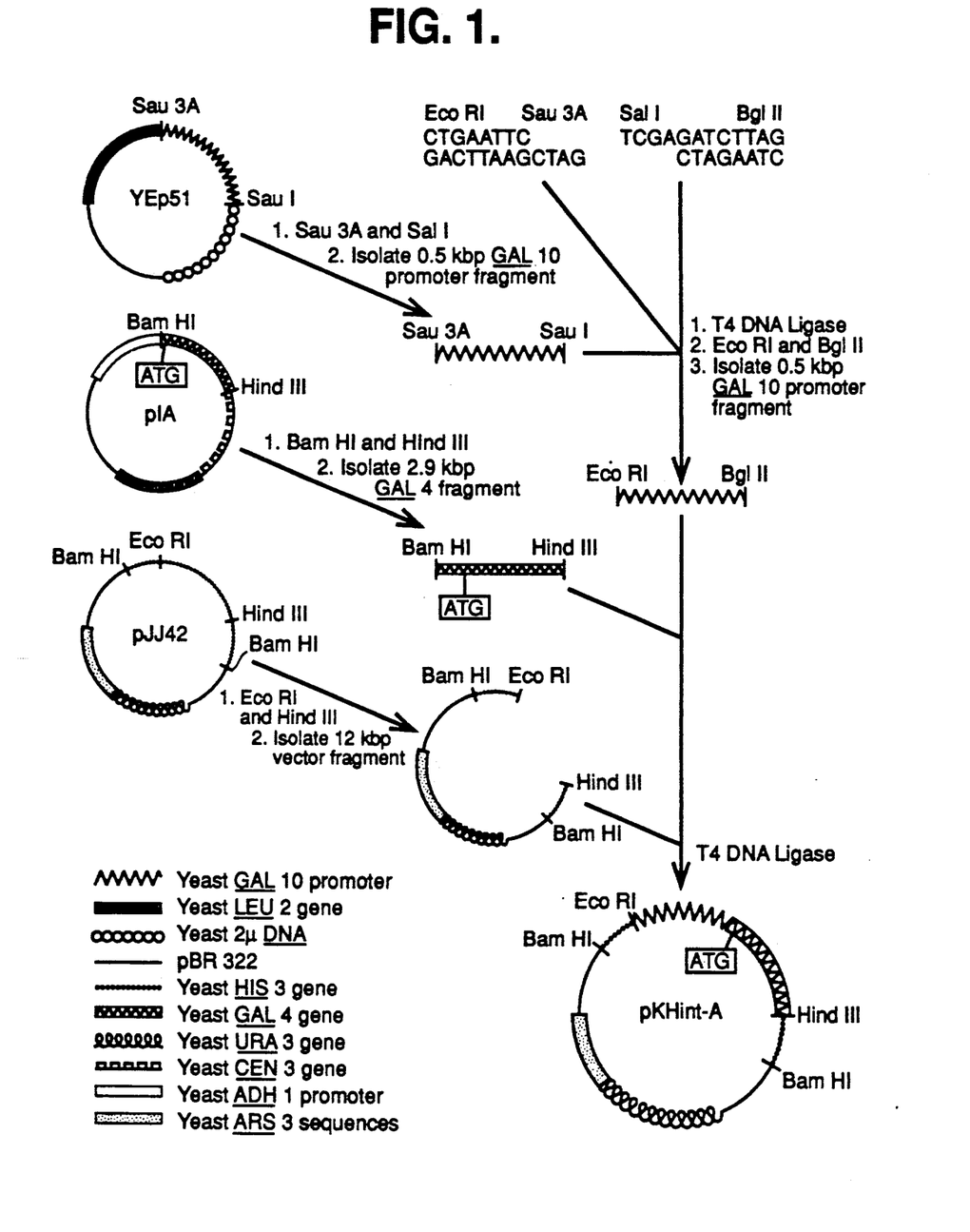
FIG. 1 depicts the preparation of pKHint-A.

The *E. coli—S. cerevisiae* shuttle vector YEp51 (Broach et al., *Experimental Manipulation of Gene Expression*, p. 83, Academic Press, 1983) contains the yeast GAL10 promoter sequences. This plasmid was digested with Sau3A and SalI, and the 0.5 kbp GAL10 promoter fragment was isolated by preparative agarose gel electrophoresis (FIG. 1, top). Two oligonucleotide linkers were synthesized and ligated to the 0.5 kbp fragment, thus converting the 5' Sau3A and the 3' SalI ends to EcoRI and BglII ends, respectively. The respective structures of these oligonucleotides are

CTGAATTC
GACTTAAGCTAG and

TCGAGATCTTAG
CTAGAATC

After subsequent digestion with EcoRI and BglII, the 0.5 kbp EcoRI-BglII GAL10 promoter fragment was isolated by preparative agarose gel electrophoresis (FIG. 1, top).

Figure 2:
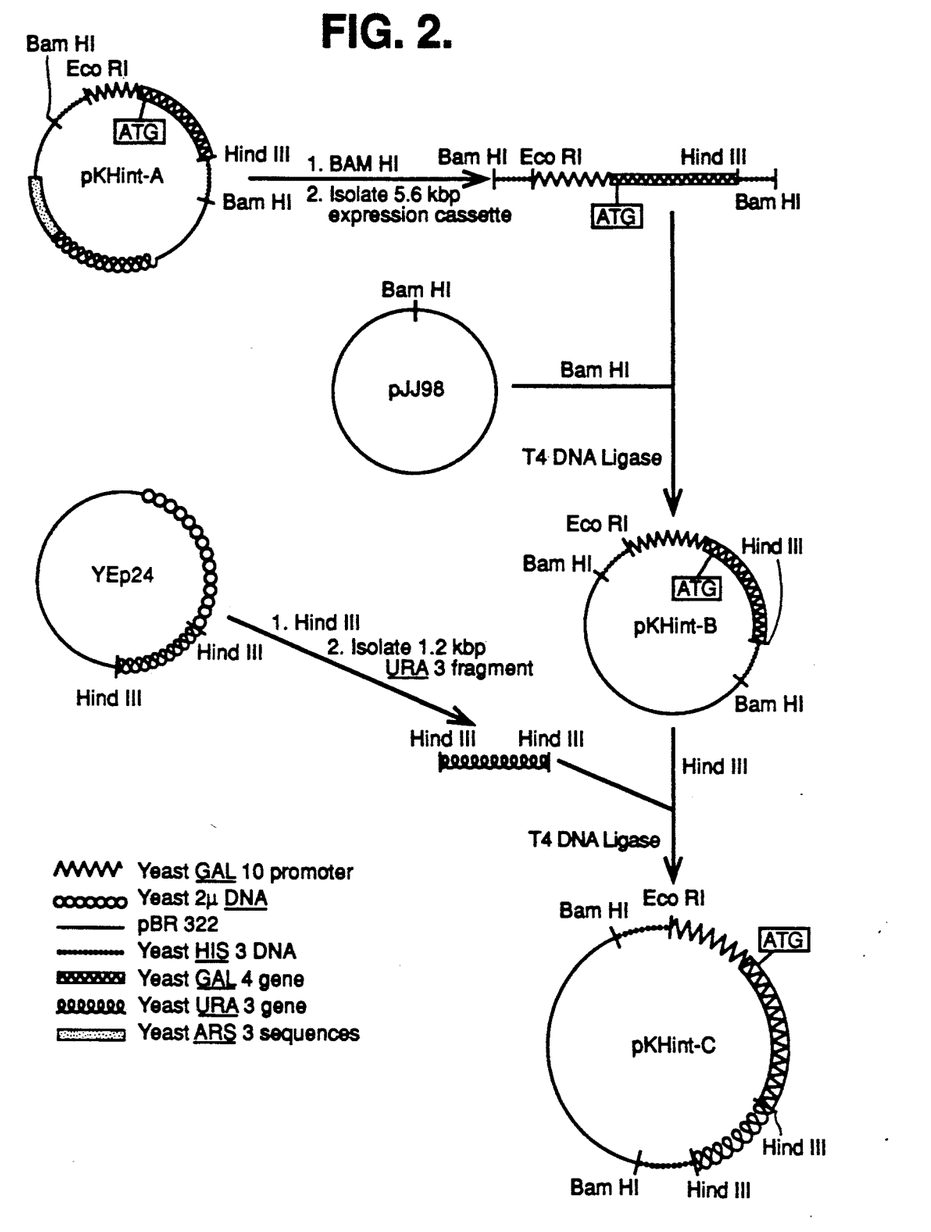
FIG. 2 depicts the preparation of pKHint-B and PKHint-C.

In order to isolate the GAL4 structural gene free of its own transcriptional control sequences, pIA (FIG. 1, middle) was constructed according to the following procedure. pYe(CEN3)41 [Clark and Carbon, Nature 287: 504 (1980)] was digested with PstI and the large fragment self-ligated to remove the LEU2 gene and reconstitute the bla gene. The resulting plasmid pYC was digested with BamHI and SalI and the large BamHI-SalI fragment was ligated with a 2.4 kbp BglII-SalI fragment bearing the yeast LEU2 gene, which had been isolated by digestion of YEp13 [Broach et al., Gene 8: 121 (1979)] with BglII and SalI. As a result of this ligation, the BamHI site is destroyed in the resulting plasmid pYCL-1. Plasmid pAAR6 (Ammerer, Methods in Enzymology 101: 192 (1983)] was digested with BamHI and HindIII, and the 1.5 kbp BamHI-HindIII fragment containing the yeast alcohol dehydrogenase I (ADHI) gene promoter was isolated. The plasmid pYCL-1 was then digested with BglII and HindIII and the resulting large vector fragment was ligated with the 1.5 kbp BamHI-HindIII ADHI promoter fragment to yield pYCLF, which does not contain a BamHI site. The GAL4 gene then was isolated from pSJ3 [Johnston and Hopper, Proc. Natl. Acad. Sci., U.S.A. 79: 6971 (1982)] by digestion with HindIII. The resulting 3.3 kbp HindIII fragment containing the GAL4 gene then was inserted into the unique HindIII site of pYCLF in the appropriate orientation, such that the ADHI promoter was upstream of the GAL4 structural gene. The resulting plasmid YCpLF+4 contains a unique BamHI site which is equidistant (approximately 0.45 kbp) from the 3'-end of the ADHI promoter and the translational start of the GAL4 gene. YCpLF+4 was cut at the BamHI site and then treated with exonuclease Bal-31 to generate various length deletions. The resulting ends were made flush-ended with the Klenow fragment of DNA polymerase I. BamHI linkers then were added and the ends religated, producing a family of plasmids with various fusions of the ADHI promoter to the GAL4 gene. Subsequent characterization of the resulting plasmids led to the isolation of a particular plasmid pIA in which the BamHI site at the 3'-end of the ADHI promoter was located five base pairs upstream of the ATG translational initiation codon for the GAL4 structural gene. The yeast GAL4 structural gene (including the translational start site) was isolated from the plasmid pIA. This plasmid was digested with BamHI and HindIII and a 2.9 kbp GAL4 fragment was isolated by preparative agarose gel electrophoresis (FIG. 1, middle). The plasmid vector pJJ42 [Struhl et al., Cold Spring Harbor Symp. Quant. Biol., 47: 901 (1982)] contains the yeast HIS3 gene. This plasmid was digested with EcoRI and HindIII which cleave within the HIS3 promoter and within the HIS3 gene, respectively. A 12 kbp vector fragment was isolated by preparative agarose gel electrophoresis and ligated simultaneously to the 0.5 kbp and 2.9 kbp fragments described above to yield the plasmid pKHint-A (FIG. 1, bottom). The pGAL10/GAL4 expression cassette was removed from pKHint-A by digestion with BamHI and isolation of the 5.6 kbp fragment by preparative agarose gel electrophoresis (FIG. 2, top). The plasmid vector pJJ98, a modified pBR322 lacking the HindIII site, was digested with BamHI and ligated to the 5.6 kbp fragment (FIG. 2, middle). The resulting plasmid pKHint-B contains a unique HindIII site located at the carboxy-terminal end of the GAL4 coding sequence. The fully functional yeast URA3 gene was isolated from the E. coli—S. cerevisiae shuttle vector YEp24 [Botstein et al., Cell 8: 17 (1979)] by digestion with HindIII and separation of the 1.2 kbp fragment by preparative agarose gel electrophoresis (FIG. 2, middle). After digestion with HindIII, plasmid pKHint-B was ligated to the 1.2 kbp HindIII fragment carrying the URA3 gene to yield pKHint-C, which now contains the complete expression cassette for integration into the yeast chromosome. The salient features of this cassette are: 1) yeast regulatable GAL10 promoter, 2) yeast GAL4 translational start site and structural gene, 3) yeast URA3 promoter and structural gene for positive selection in ura3⁻ yeast host, 4) two BamHI sites which cleave within the 5' and 3' nontranslated sequence of the HIS3 gene for integrative transformation into the yeast HIS3 chromosomal locus.

EXAMPLE 2

Figure 3:
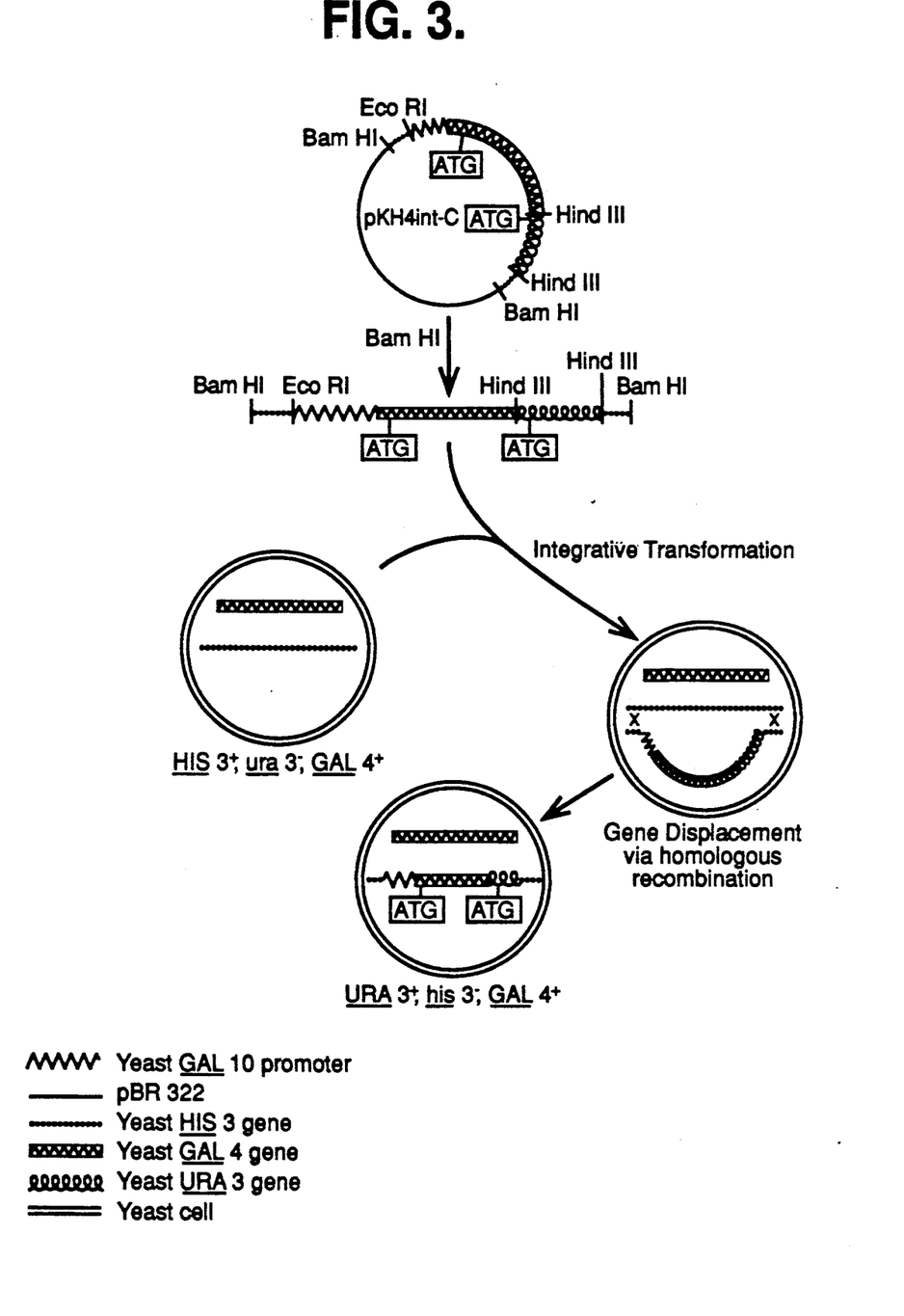
FIG. 3 depicts the preparation of Sc252(pGAL10-/GAL4) and Sc294(pGAL10/GAL4).

Preparation of novel yeast strains containing an integrated pGAL10/GAL4 expression cassette When digested with BamHI, the plasmid pKHint-C yielded a 6.8 kbp expression cassette flanked on either end by nontranslated HIS3 DNA sequences (FIG. 3, top). The digested DNA was used to transform S. cerevisiae host strains Sc252 (MATa, ura3-52, leu2-2-112, ade1, MEL1) [Johnson et al., Proc. Natl. Acad, Sci. U.S.A., 79: 697 (1982)] and Sc294 (Matα, ura3-52, leu2-2-112, Δgal1-10-7, MEL1). Acting as a targeting device, the BamHI ends directed the expression cassette to the chromosomal HIS3 locus where the cassette integrated via homologous recombination (FIG. 3, middle). Transformants were selected for URA3+ and screened for his3⁻. Southern blot analysis of the clonal isolates confirmed that the cassette had integrated at the HIS3 locus. Transformants and their respective parental strains were grown in synthetic selective (leu⁻) glycerol-lactic acid medium [Sherman et al., Methods in Yeast Genetics. A Laboratory Manual, Cold Spring Harbor Press (1979)], either with or without 2% (w/v) galactose. After harvesting at $A^{600}=1.5$, RNA extracts were prepared [Zitomer et al., Proc. Natl. Acad. Sci. U.S.A. 76: 627 (1979)] and analyzed by Northern blot techniques. [Thomas, Proc. Natl. Acad. Sci. U.S.A. 77: 5201 (1980)]. In the presence of galactose, transcription of GAL4 mRNA is observed to be at least 20-fold enhanced in the Sc252 (pGAL10/GAL4) and Sc294 (pGAL10/GAL4) strains over their respective parental strains. The strains show basal-level expression of GAL4 mRNA in the absence of galactose. Thus, the novel yeast strains display the desired phenotype of basal-level GAL4 expression in the absence of galactose and much higher (than wild-type strains) level expression of GAL4 in the presence of galactose.

EXAMPLE 3

Figure 4:
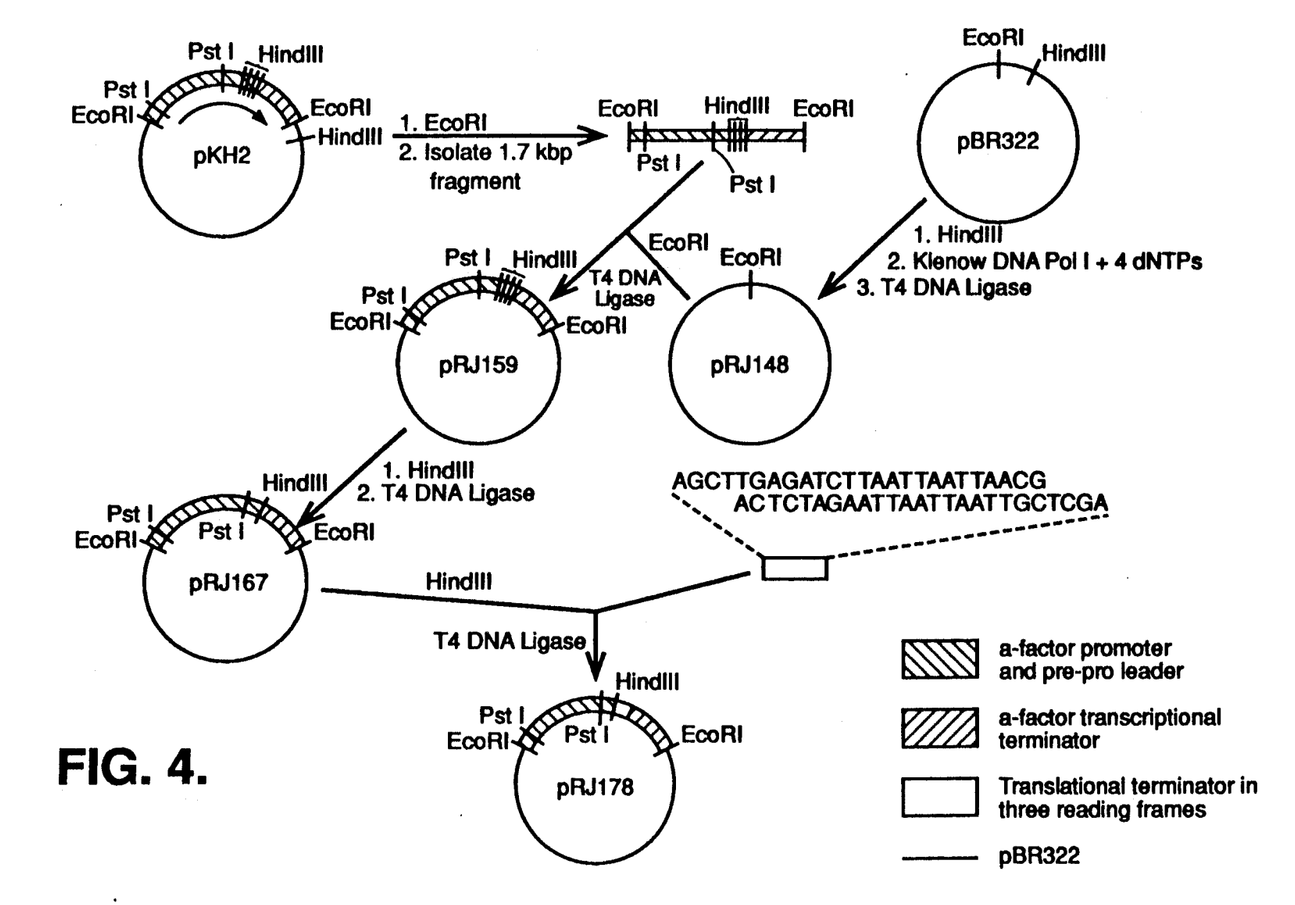
FIG. 4 depicts the preparation of PRJ178.
Figure 5:
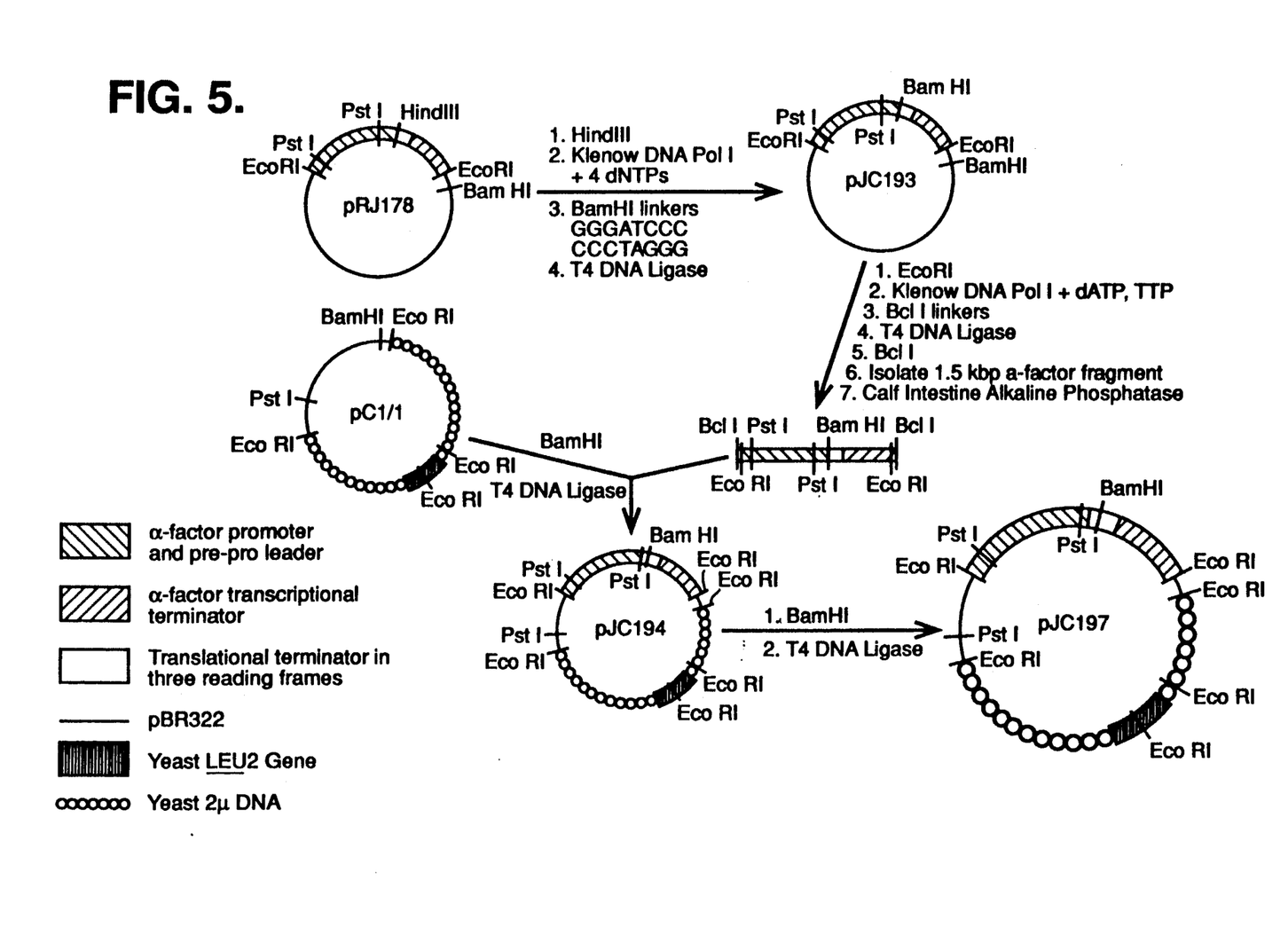
FIG. 5 depicts the preparation of pJC197.
Figure 6:
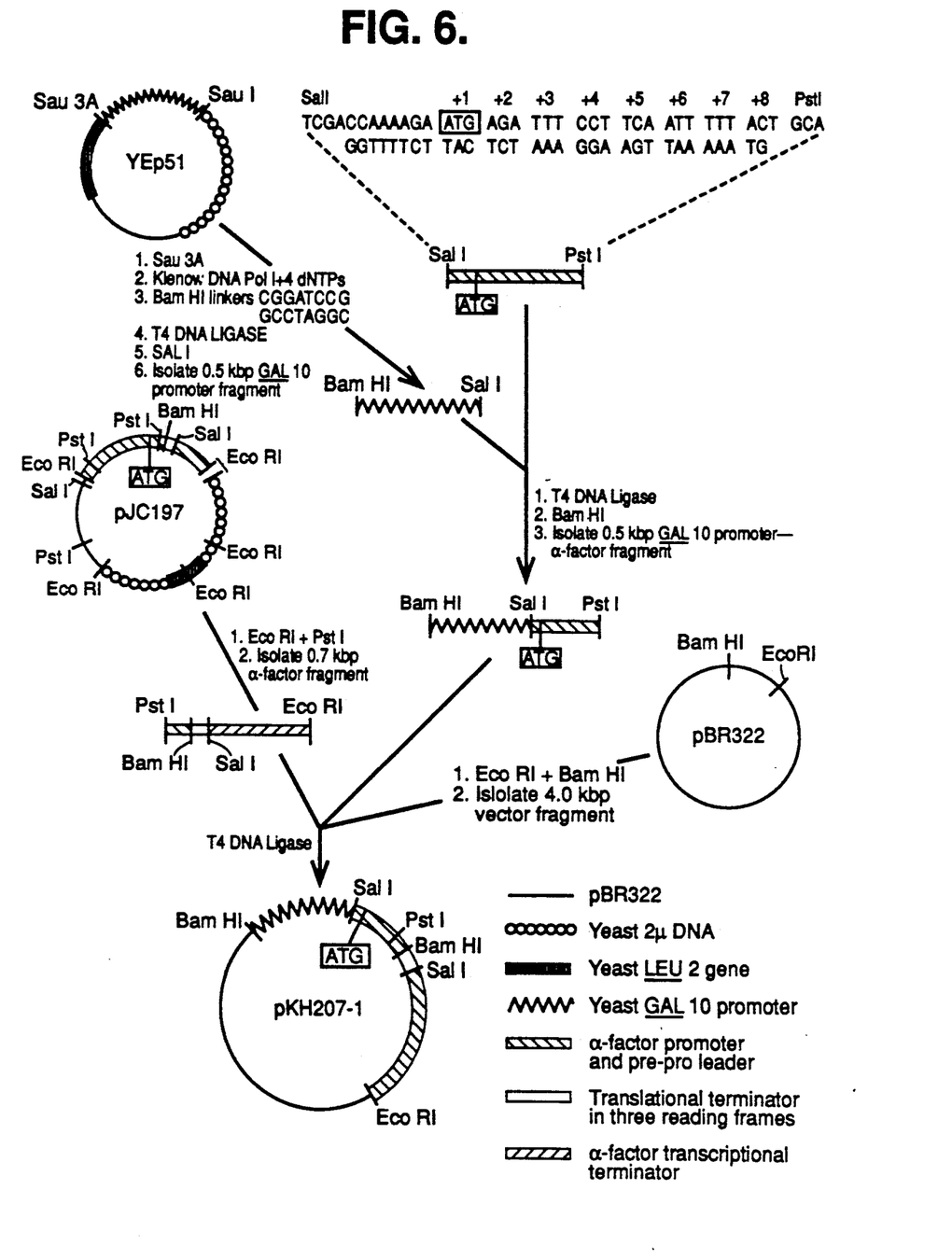
FIG. 6 depicts the preparation of pKH207-1.

Preparation of an expression vector with a GAL10 promoter directing expression of EBMA The alpha mating factor (α factor) gene MFα1 was cloned onto a plasmid vector from S. cerevisiae genomic DNA [Kurjan et al., Cell 30: 933 (1982); Singh et al., Nucleic Acids Res. 11: 4049 (1983)]. The resulting plasmid pKH2 was digested with EcoRI and the 1.7 kbp fragment bearing the alpha mating factor gene was purified by preparative agarose gel electrophoresis (FIG. 4, top). Plasmid pRJ148 (a modified pBR322 lacking the HindIII site) was digested with EcoRI and ligated to the 1.7 kbp fragment to yield the plasmid pRJ159 (FIG. 4, middle). This DNA was digested with HindIII and self-ligated to form plasmid pRJ167, which now has a unique HindIII site (FIG. 4, middle). Plasmid pRJ167 was digested with HindIII and modified by the insertion of a synthetic oligonucleotide adaptor to yield a new plasmid (pRJ178) containing a unique HindIII site which is to the 3' side of the promoter and pre-pro-leader and to the 5' side of the translational termination signals in all three reading frames (FIG. 4, bottom). The HindIII site was converted to a BamHI site by digestion with HindIII, flush-ending with the Klenow fragment of DNA polymerase I, addition of BamHI linkers and self-ligation to form plasmid pJC193 (FIG. 5, top). This plasmid was digested with EcoRI, flush-ended with the Klenow fragment of DNA polymerase I, modified by the addition of BclI linkers, digested with BclI, and the 1.5 kbp fragment bearing the alpha mating factor gene isolated by preparative agarose gel electrophoresis (FIG. 5, middle). This resulting BclI fragment then was treated with calf intestine alkaline phosphatase and inserted into the unique BamHI site of pCl/1, destroying the original BamHI site in the process (plasmid pJC194; FIG. 5, bottom). This DNA was digested with BamHI and self-ligated to remove excess BamHI linkers (plasmid pJC197, FIG. 5, bottom).

pJC197 was digested with EcoRI and PstI. A 0.7 kbp fragment containing a portion of the alpha mating factor pre-pro-leader, a three-frame translational terminator and the alpha mating factor transcriptional terminator was isolated by preparative agarose gel electrophoresis (FIG. 6, middle left). The E. coli—S. cerevisiae shuttle vector YEp51 contains the yeast GAL10 gene promoter sequences. This DNA was digested with Sau3A, made flush-ended with the Klenow fragment of DNA polymerase I, and ligated with synthetic BamHI linkers of the structure:

```
CGGATCCG
GCCTAGGC
```

The linkered DNA was digested with SalI and a 0.5 kbp GAL10 promoter fragment was isolated by preparative agarose gel electrophoresis (FIG. 6, top left). A 35 bp SalI - PstI synthetic oligonucleotide adapter was synthesized, having the structure:

TCGACCAAAAGAATGAGATTTCCTTCAATTTTTACTGCA
GGTTTTCTTACTCTAAAGGAAGTTAAAAATG

Figure 7:
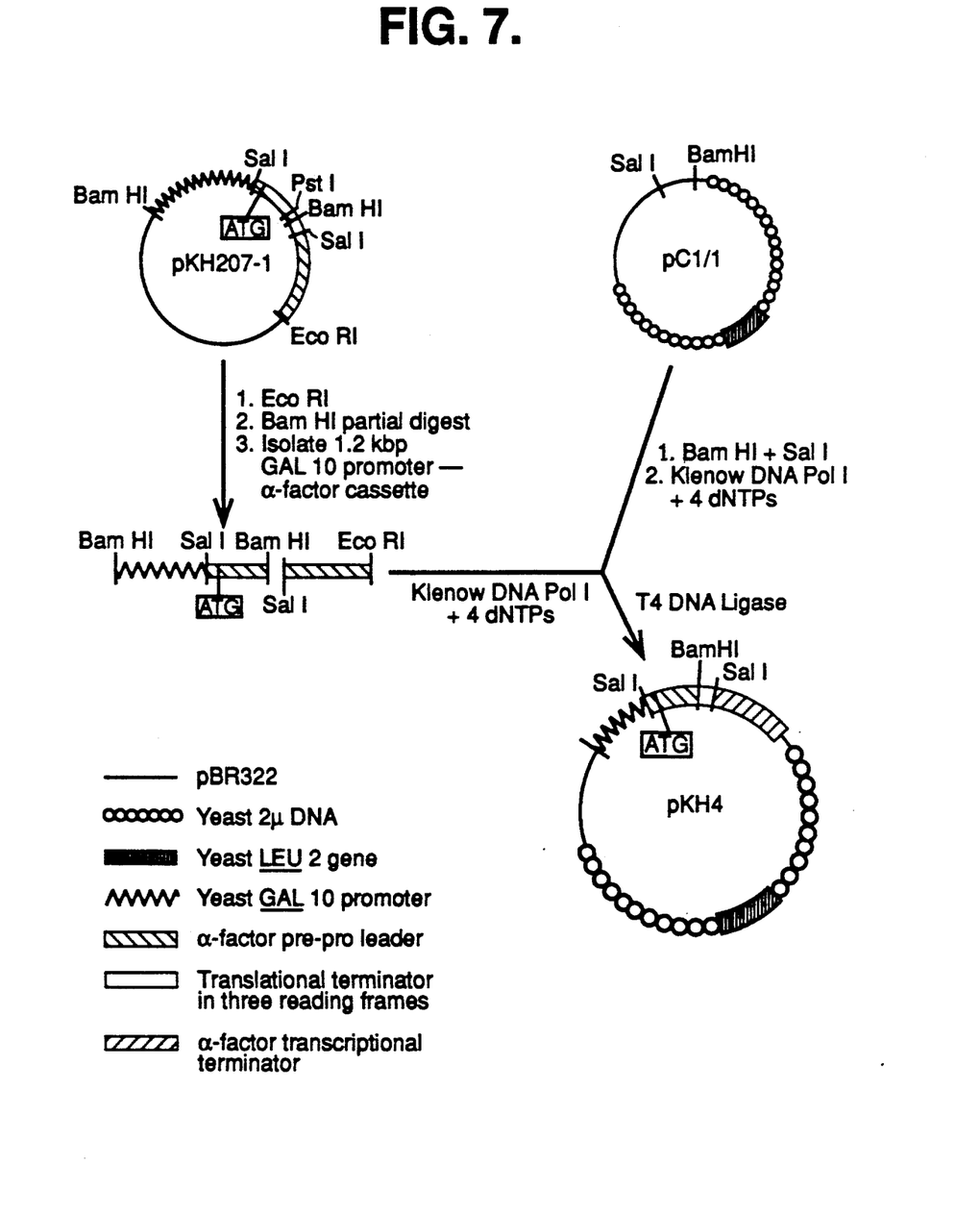
FIG. 7 depicts the preparation of pKH4.

This adapter contains 11 base pairs of the alpha mating factor non-translated leader and the ATG and first 8 amino acids of the alpha mating factor pre-pro-leader. The 0.5 kbp GAL10 promoter and the 35 bp adapter fragments were ligated together and digested with BamHI to generate a 5' BamHI end. The resulting 0.5 kbp BamHI-PstI GAL10 promoter-alpha mating factor fragment was isolated by preparative agarose gel electrophoresis (FIG. 6, middle). The plasmid vector pBR322 was digested with EcoRI and BamHI, and a 4.0 kbp vector fragment was isolated by preparative agarose gel electrophoresis. The 4.0 kbp, 0.7 kbp and 0.5 kbp fragments were ligated together to create the plasmid pKH207-1 (FIG. 6, bottom left). pKH207-1 was digested to completion with EcoRI and partially digested with BamHI. The 1.2 kbp BamHI - EcoRI GAL10 promoter-alpha mating factor expression cassette was isolated by preparative agarose gel electrophoresis and made flush-ended with the Klenow fragment of DNA polymerase I (FIG. 7, middle). The E. coli—S. cerevisiae shuttle vector pCl/1 [Beggs, Nature 275: 104 (1978); Rosenberg et al., Nature 312: 77 (1984)] was digested with BamHI and SalI, made flush-ended with the Klenow fragment of DNA polymerase I, and ligated with the 1.2 kbp cassette to create a new expression plasmid, pKH4 (FIG. 7, bottom right).

Figure 8:
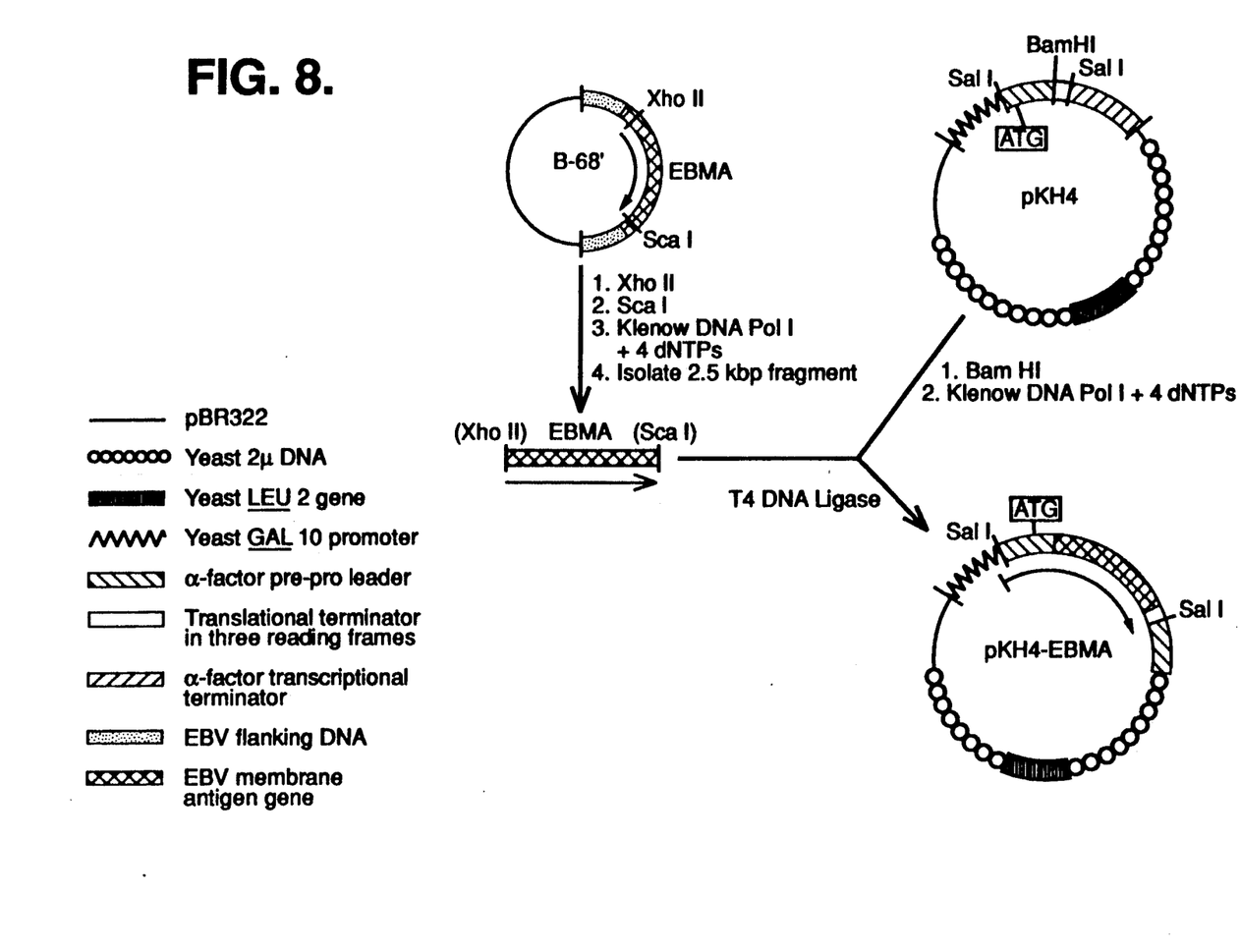
FIG. 8 depicts the preparation of pKH4-EBMA.

The B68' plasmid [Hummel et al., J. Virol. 49: 413 (1984)] carrying the BamHI-L DNA fragment containing the EBMA gene was digested with XhoII and ScaI, and the 2.5 kbp fragment containing the EBMA structural gene was made flush-ended with the Klenow fragment of DNA polymerase I (FIG. 8, top). The expression vector pKH4 was digested with BamHI and made flush-ended with the Klenow fragment of DNA polymerase I. The 2.5 kbp EBMA fragment was ligated to the vector. This recombinant plasmid pKH4-EBMA (FIG. 8, bottom) has the following salient features: (1) E. coli-derived sequences for the selection and amplification of the plasmid in E./coli, (2) S. cerevisiae-derived sequences for the selection and amplification of the plasmid in yeast, (3) yeast GAL10 promoter, (4) yeast alpha mating factor pre-leader for directing the translational product into the rough endoplasmic reticulum, (5) yeast alpha mating factor pro-leader which encodes N-glycosylation signal sequences and which is cleaved by the KEX2 and STE13 proteases (gene products) [Julius et al., Cell 32: 839 (1983); Julius et al., Cell 37: 1075 (1984)], (6) the coding sequence for EBMA, (7) a translational termination sequence, and (8) a transcriptional termination sequence.

EXAMPLE 4

Expression of the EBMA gene in novel yeast strains containing an integrated pGAL10/GAL4 expression cassette The expression vector pKH4-EBMA (FIG. 8, bottom) was introduced to S. cerevisiae strains Sc252, Sc252 (pGAL10/GAL4) and Sc294 (pGAL10/GAL4). The transformants (with pKH4-EBMA) were grown in synthetic selective glycerol-lactic acid medium to $A^{600}=0-.5-1.0$, at which time galactose was added to a final concentration of 2% (w/v). Lysates were prepared, electrophoresed in polyacrylamide gels and Western blotted to nitrocellulose. The 375,000 and 225,000 and 175,000 dalton proteins were found to be specific to EBMA by virtue of their presence only in transformants, their reactivity with human convalescent EBV sera and an EBMA-specific monoclonal antibody [Qualtiere et al., Proc. Natl. Acad. Sci. 79: 616 (1982)], and their lack of reactivity with pooled negative human sera. No EBMA-specific proteins were detected in cultures grown in the absence of galactose. At 24 hours after the addition of galactose, the 2 strains Sc252 (pGAL10/GAL4) and Sc294 (pGAL10/GAL4) each contain 10-fold more EBMA-specific proteins than does strain Sc252.

What is claimed is:

1. A strain of species of the families Saccharomycetaceae or Cryptococcaceae wherein the chromosome is modified by integration of a hybrid gene comprised of a galactose-inducible promoter linked to the gene for a positive regulatory protein which serves as the transcriptional activator of galactose-inducible promoters, said strain being the host for a plasmid comprising a galactose-inducible promoter linked to a heterologous gene whose expression is driven by the galactose-inducible promoter.

2. A strain according to claim 1, wherein the host is a species of the genus Saccharmoyces.

3. A strain according to claim 2, wherein the host is Saccharomyces cerevisiae.

4. A strain according to claim 1, wherein the galactose-inducible promoter linked to the gene for the yeast positive regulatory protein is GAL-10.

5. A strain according to claim 1, wherein the gene for the positive regulatory protein is GAL4.

6. A strain according to claim 1, wherein the galactose-inducible promoter is GAL1, GAL2, GAL7, GAL10, or MEL1.

7. A method of expressing a desired heterologous protein comprising growing in a nutrient medium a strain of species of the families Saccharomycetaceae or Cryptococcaceae wherein the chromosome is modified by integration of a hybrid gene comprised of a galactose inducible promoter linked to the gene for a positive regulatory protein which serves as the transcriptional activator of galactose-inducible promoters, said strain being the host for a plasmid comprising a yeast galactose-inducible promoter linked to a heterologous gene whose expression is driven by the galactose-inducible promoter.

8. A method according to claim 7, wherein the host is a species of the genus Saccharomyces.

9. A method according to claim 8, wherein the host is Saccharomyces cerevisiae.

10. A method according to claim 7, wherein the galactose inducible promoter linked to the gene for the yeast positive regulatory protein is GAL10.

11. A method according to claim 7, wherein the gene for the positive regulatory protein is GAL4.

12. A method according to claim 7, wherein the galactose-inducible promoter is GAL1, GAL2, GAL7, GAL10, or MEL1.

* * * * *